United States Patent [19]

Tung

[11] Patent Number: 5,053,386

[45] Date of Patent: Oct. 1, 1991

[54] ORALLY ADMINISTRABLE ANTI-METASTATIC LECTIN COMPOSITIONS AND METHODS

[76] Inventor: Ta C. Tung, 210 Lindbergh Ave., Broomall, Pa. 19008

[21] Appl. No.: 529,742

[22] Filed: May 23, 1990

Related U.S. Application Data

[63] Continuation of Ser. No. 173,826, Mar. 28, 1988, abandoned.

[30] Foreign Application Priority Data

Jul. 24, 1987 [TW] Taiwan ............................. 76103632
Aug. 19, 1987 [TW] Taiwan ............................. 76104897

[51] Int. Cl.$^5$ ............... A01N 37/18; A61K 37/02; A61K 35/78
[52] U.S. Cl. ............................ 514/2; 424/195.1; 530/396
[58] Field of Search ................ 514/2; 424/195.1; 530/396

[56] References Cited

PUBLICATIONS

Dyer "An Index of Tumor Chemotherapy" National Cancer Institute, NIH, Mar. 1949, p. 175.

Chabner, et al. "Clinical Pharmacology of Cancer Chemotherapy" taken from Chapter 9 of Cancer, Principles and Practice of Oncology, Lippincott Co., Philadelphia, 1982, pp. 158-159.

Tung, T. C. et al., J. Chinese Oncol. Soc., 3(3) 1-8 (1987), Inhibitory Effect by Orally Administered Abrus Agglutinin on the Anti-Metastasis of Sarcoma-180 and B-16 Melanoma.

*Primary Examiner*—Nathan M. Nutter
*Attorney, Agent, or Firm*—Weiser & Stapler

[57] ABSTRACT

Compositions and methods of treatment comprising the lectins Abrin and Abrus agglutinin for the suppression of post-surgical malignant tumor metastasis are disclosed. Also disclosed is the administration of compositions and methods of treatment utilizing the above lectins in combination with either or both radiation treatment and/or chemotherapy.

20 Claims, No Drawings

ORALLY ADMINISTRABLE ANTI-METASTATIC LECTIN COMPOSITIONS AND METHODS

This application is a continuation of application Ser. No. 173,826, filed Mar. 28, 1988, now abandoned.

BACKGROUND OF THE INVENTION

1. Field of the Invention

This invention relates to the oral dosage forms of lectins and the medicinal use of these preparations, especially of Abrin and Abrus agglutinin for the suppression of post-surgical malignant tumor metastasis. This invention also relates to a method of treatment comprising the daily oral administration of Abrin and Abrus agglutinin post-surgically, in conjunction with and/or subsequent to, radiation therapy and/or chemotherapy to suppress malignant tumor metastasis.

This invention further relates to oral dosage compositions of Abrin and Abrus agglutinin with no other active agent, or in combination with a cancer chemotherapy agent for a post-surgical lectin treatment in conjunction with chemotherapy.

Traditionally, lectins have been administered to cancer patients parenterally, a treatment that had to be performed by physicians in a hospital. The clinical use of lectins has been hindered by this requirement that lectin compositions be administered to a cancer patient in a hospital under direct physician supervision. There is also an element of risk involved with the parenteral administration of a drug.

There exists, therefore, a great need for safer, orally-administerable lectin compositions that a cancer patient can self-administer without direct physician supervision, to expand the clinical use of these compositions. As described in greater detail hereinafter, the compositions of this invention comprise lectins in an orally-administerable form demonstrating significant anti-cancer effects, especially in the inhibition of metastasis.

2. Objects of the Invention

The invention provides orally administerable anti-metastaic lectin compositions and methods of treatment, which have numerous practical applications for the suppression of malignant tumor metastasis. The invention provides a valuable contribution to the post-surgical treatment of cancer. The invention provides a safe, oral composition, easy to administer to a cancer patient without direct physician intervention. The invention provides a method of treatment for the post-surgical suppression of malignant tumor metastasis by the daily oral administration of lectin compositions in conjunction with and/or subsequent to chemotherapy and/or radiation treatment. The invention provides lectin compositions with no other active agent, or in combination with a cancer chemotherapy agent for a post-surgical lectin treatment in conjunction with chemotherapy.

Thus, an important object of the invention is to provide safe, orally-administerable lectin compositions which are effective in the suppression of malignant tumor metastasis and may be taken by a cancer patient without direct physician supervision.

Another object of the invention is to provide a post-surgical method for daily administering oral lectin compositions to a cancer patient in amounts effective to suppress malignant tumor metastasis. It is a further object of the invention to provide a method of treating a cancer patient with lectins to suppress malignant tumor metastasis in conjunction with and/or subsequent to radiation therapy and/or chemotherapy.

It is also an object of the invention to provide oral compositions wherein a lectin is the sole active ingredient as well as compositions wherein a lectin is combined with a cancer chemotherapy agent for lectin therapy in conjunction with chemotherapy.

The listing of objectives provided herein, or of features of the invention, is not intended to be exhaustive, but merely illustrative.

Other objects will become apparent to one of average skill in the art in the further description of the invention.

3. Brief Description of the Prior Art

Lectins are cell agglutinating proteins having specific affinity for a wide variety of carbohydrates. Many plants, e.g., beans, vegetables and medicinal herbs, contain various lectins in their seeds, leaves and bark, etc. (1). Phyto-hemaglutinin (PHA), Concanavalin-A (Con-A), Abrin, Abrus agglutinin (AAG), Ricin, Ricinus agglutinin, soybean agglutinin and wheat germ agglutinin are among the well-known lectins being isolated from plants. These glycophilic proteins have a specific affinity for carbohydrates and bind to the terminal monosaccharide moiety of cell membrane receptors (2). Consequently, capping occurs (3) followed by endocytosis.

Lectins enter into the cytoplasm, and elicit biological responses, for example; 1) induction of lymphokines such as interferons (4,5), 2) stimulation of DNA synthesis followed by mitogenic cell division (6), and 3) after entering the cells, suppression of protein and DNA synthesis (7). Lectins have been suggested to inhibit tumor or cancer cell development in vitro either directly, by mediation of macrophages or by activation of T lymphocytes (8-10). In vivo anti tumor effects of lectins has been demonstrated in animals after parenteral administration (11-13), but the use of orally administered lectins has not been reported in the literature. It has been further shown that a portion of the orally administered lectins bind to membrane receptors of lymphocytes on the gastro-intestinal walls and entered the body. Therefore, lectins in food, which have not been destroyed during cooking or digestion, are absorbed via the lymphatic system of the digestive tract, and exert their specific biological functions. It has also been demonstrated that Abrus agglutinin (AAG) and Abrin, isolated from seeds of Abrus precatorius induce r-interferons and consequently increase immunities against cancer (5).

Other prior art references considered in the preparation of this application include Lin, 1969 (15); Post, 1980 (16); Wang, 1982 (17) and Sharon and Lis, 1975 (18).

SUMMARY OF THE INVENTION

The invention comprises orally administerable lectin compositions effective in the post-surgical suppression of malignant tumor metastasis.

The invention comprises a method for the oral administration of lectin compositions for the post-surgical suppression of malignant tumor metastasis. In accordance with the invention, this method can be performed in conjunction with and/or subsequent to radiation therapy and/or chemotherapy.

In accordance with the invention the compositions of the invention may comprise a lectin as the sole active ingredient, or the lectin may be combined with a cancer chemotherapy agent for the administration of lectin treatment in conjunction with chemotherapy.

DETAILED DESCRIPTION OF THE INVENTION

As stated above, it has been discovered that orally administered AAG or Abrin have significant anti-cancer effects, especially in the post-surgical inhibition of malignant tumor metastasis.

AAG and Abrin are lectin proteins having molecular weight of 130,000 and 65,000, respectively. It has been discovered that orally administered AAG and Abrin are biologically active. Mice, after receiving oral doses of AAG or Abrin, showed an increase in peripheral leucocytes as well as T-lymphocytes and the induction of r-interferon (5). These observations prove the absorption of orally administered AAG, Abrin and other lectins. It is more convenient and safer to administer orally than parenterally by physicians in the hospital.

Many lectins are normal constituents of plants and vegetables, that are safe, edible and non-toxic. Lectins are destroyed, if cooked. In order to preserve their biological activities, lectins should be extracted from the plants and processed to oral dosage forms.

The biological effects of orally administered lectins have been demonstrated.

A mg dose of the lectin Con-A-FITC was administered to six mice that were sacrificed 1.5 to 2.0 hours later. Examination of cryogenic sections of the G.I. tracts under fluorescent microscope showed fluorecineited lymphocytes in the areas of cilia, Payer's patch, and laminar propria of the G.I. tracts.

In another study mice receiving daily oral dose of AAG (200 ng) or Abrin 20 ng) and S-180 tumor cells ($1-2\times10^6$) (14) via tail vein injection, had significantly lower incidence of death and of tumor metastasis to the lung than the control group, when mice were examined three weeks after the treatment. Some AAG or Abrin treated mice even recovered from cancer (See Table I and FIG. 1-8).

It was unexpected that the lectin orally administered to mice would be bioavailable and would be effective in the suppression of tumor metastasis.

The suppression of tumor metastasis has been demonstrated to occur at a greater rate with the administration of lectins in conjunction with and/or subsequent to chemotherapy and/or radiation treatment than occurs with chemotherapy and/or radiation treatment alone. Daily administration of lectins have also resulted in increased immunity (4–6).

The compositions of the invention, prepared by the method described in this application are administered orally on a daily basis to a post-operative cancer patient to suppress malignant tumor metastasis.

The compositions are administered daily over a course of treatment until a patient is adjudged to be free of cancer, generally five years.

The composition of the invention generally comprises a quantity of lectin equivalent to the unit dosage for the day. However, less quantities may be used with multiple administrations over the course of the day.

For either AAG or Abrin the minimum daily dosage is that smallest quantity effective in the suppression of cancer tumor metastasis, generally about 10 nanograms. The effectiveness of AAG increases as the daily dosage increases, up to about 500 micrograms. Daily dosages in excess of this quantity do not demonstrate any increased effectiveness in the suppression of cancer tumor metastasis. The preferred daily dosage is between about 50 and about 200 nanograms.

The effectiveness of Abrin increases as the daily dosage increases, up to about 20 nanograms. Daily dosages in excess of this quantity do not demonstrate any increased effectiveness in the suppression of cancer tumor metastasis. The preferred daily dosage is between about 2.0 and about 5.0 nanograms.

When, in addition to the radiation and chemotherapy, patients suffering from various types of cancer were given post-surgical daily oral doses of AAG (200 microgram) or Abrin (5 microgram), suppression of cancer recurrence was apparent after one year observation.

Lectins, in oral dosage forms prepared by the method described in this invention, could thus be given to humans as daily post-operative cancer treatment supplement.

In another embodiment of the invention, the compositions of the invention are administered on a daily basis to a post-operative cancer patient in conjunction with and/or subsequent to radiation therapy or chemotherapy to suppress malignant tumor metastasis.

In still another embodiment of the invention, the compositions administered comprise a lectin and a cancer chemotherapy agent for the administration of lectins in conjunction with chemotherapy treatment on a daily basis to a post-operative cancer patient to suppress malignant tumor metastasis. Suitable oral cancer chemotherapy agents include alkylating agents such as cyclophosphamide, melphalan, busulfan, and chlorumbucil; anti-metabolites such as methotrexate, 6-Mercaptopurine and 6-Thioguanine, androgens such as ethinyl estradiol, progestins such as 6-Methylhydroxy progesterone, thyroid hormone, adrenal cortical compounds such as prednisone and dexamethasone, and other compounds such as procarbazine, CCNU, MeCCNU, o,p'-DDD, hexamethylmelanine, and hydroxyurea. It is contemplated by this embodiment that lectins be compounded with the oral chemotherapy agents disclosed in Harrison, *Principles of Internal Medicine,* Ch. 323, pp. 1745–1767 (8th ed., McGraw-Hill, New York 1977), which is incorporated herein by reference.

It is within the scope of the present invention that lectins be administered to a post-operative cancer patient in a separate composition in conjunction with a cancer chemotherapy agent. In one embodiment the composition containing lectin is administered to the patient immediately before or after the administration of the cancer chemotherapy agent and/or radiation treatment. In another embodiment, the administration of the therapies is altered so that several minutes or hours pass between their administration. In yet another embodiment, the lectin treatment is not initiated until the patient's course of radiation treatment and/or chemotherapy is completed.

It is also within the scope of the invention that a pharmaceutical composition containing a lectin be administered to an individual other than a post-operative cancer patient. The composition can also be administered to individuals in which it is desired to increase the strength of their immune systems, particularly those who have contracted or are at risk for cancer, AIDS or hepatitis, or who have tested positive to an antigen test establishing their exposure to AIDS or hepatitis.

In other aspects, the composition of the invention may contain conventional materials and ingredients and conform to pharmacologically accepted formulations. In preparing the desired pharmaceutical form of the present compositions, various additives, diluents and adjuvants can e utilized.

The following examples are not intended to limit the invention, but are merely illustrative thereof. It is understood that one of average skill in the art would be able to make substitutions, change proportions, make other variations, all within the scope of the teachings, and without undue experimentation.

EXAMPLE 1

Method of Preparation of the Oral Dosage Forms of Lectins

A 500g quantity of soybeans were ground to powder, extracted with water, and further purified by ammonium sulfate fractional precipitation. Lectins in the fractions of 30 to 70% ammonium sulfate saturation were re-isolated by adsorption on a sugar affinity column and followed by final purification on a Sephadex column. Purified lectins thus obtained were lyophilized to dry powder. Casein was added as excipient to prepare dosage forms.

EXAMPLE 2

Preparation of AAG and Abrin Oral Dosage Forms

After washing with hexane to remove lipids from the seeds of Abrus precatorius, the seeds were ground to powder which was then extracted with water. Ammonium sulfate was then added in portions to aqueous extracts to fractionally precipitate lectins. The precipitates from 35-70% saturation were dissolved in water and dialyzed. After dialysis, Sepharose was added and stirred for 4 hours in a cold room. Lectins adsorbed on Sepharose were separated by centrifugation, washed with water three times, and then re-suspended in 2% solution of galactose for 3 hours. Sepharose was removed by centrifugation and the aqueous layer containing AAG and Abrin was chromatographed over a Sephadex column which separated AAG from Abrin. The aqueous fractions of AAG and Abrin were then lyophilyzed to obtain pure AAG or Abrin. Casein was used as excipient to prepare dosage forms.

EXAMPLE 3

Comparison of Oral vs. Parenteral Administration of AAG in Mice

A 200 nanogram per day dose of AAG was administered subcutaneously to each of 20 mice for four days. On the fifth day, the mice intravenously via the tail vein each received $2.5 \times 10^6$ cells of Sarcoma-180. A control group of mice each received the same quantity of S-180 without having first received AAG. Both groups were sacrificed after three weeks and microscopic pathological examination of pulmonary metastasis was conducted.

Of the test group that had received AAG, 50% exhibited no metastasis; 33% had first grade metastasis; none had second grade metastasis; and 17% had third grade metastasis. Of the control group, 25% exhibited no metastasis; 13% had first grade metastasis; 25% had second grade metastasis; and 37% had third grade metastasis.

A third group of 20 mice each received a daily 200 nanogram/day oral dose of AAG for one week. On the eighth day, the mice, intravenously via the tail vein each received $2.5 \times 10^6$ cells of S-180. A control group of mice each received the same quantity of S-180 without having first received AAG. The test group mice each continued to receive a 200 nanogram/day oral dose of AAG for the next seven days. Both groups were sacrificed after three weeks and microscopic pathological examination of pulmonary metastasis was conducted.

The test group and the control group results differed significantly ($p<0.05$). The test group averaged $0.2\pm0.4$ metastatic cancer nodules. The control group averaged $31.4\pm42.4$ metastatic cancer nodules.

|  | Incidency of Pulmonary Metastasis | |
| --- | --- | --- |
|  | Control gr. | Test gr. |
| visible exam. | 17/20 (85%) | 4/20 (20%) |
| pathological exam. | 14/20 (70%) | 1/20 (5%) |

The incidency of pulmonary metastasis of S-180 cells in the AAG and administration test and control groups is shown in Table I.

This example establishes that the oral administration of AAG is equally as effective at suppressing cancer cell metastasis as the parenteral administration of AAG.

EXAMPLE 4

Comparison of Oral vs. Parenteral Administration of AAG in Mice

AAG was administered subcutaneously to a test group of nine $C_{57}BL_6$ mice as in Example 3 above. On the fifth day $2\times 10^4$ B-16 melanoma cells were administered intravenously via the tail vein to each of the test group and a control group of nine, which had received no AAG. Both groups were sacrificed and examined as in Example 3.

The test group and the control group results differed significantly ($p<0.05$). The test group averaged $23.6\pm13.0$ metastatic cancer nodules. The control group averaged $44.0\pm23.6$ metastatic cancer nodules.

A third group of seven mice was orally administered AAG as in Example 3 above. On the eighth day $2\times 10^4$ B-16 melanoma cells were administered intravenously via the tail vein to each of the test group and to eight mice in the control group, which had received no AAG. The test group mice each continued to receive a daily dose of 200 nanograms AAG until the third week, when both groups of mice were sacrificed and examined as in Example 3.

The test group and control group results again differed significantly ($p<0.05$). The test group averaged $4.1\pm5.0$ metastatic cancer nodules. The control group averaged $14.9\pm7.4$ metastatic cancer nodules.

This example further establishes that the oral administration of AAG is equally as effective at suppressing cancer cell metastasis as the parenteral administration of AAG.

The significance of this invention is that the orally administered lectins, especially AAG, Abrin and Con-A are useful for the treatment and prevention of cancer, by binding to the membrane receptor of lymphocytes on the G.I. wall, and entering the body, eliciting anticancer activities, before being digested by proteolytic enzymes. The oral uses of lectins are safer and more convenient than parenteral uses. The oral lectins are as effective as parenteral lectins for anticancer uses. Convenience is another important advantage of the oral forms.

In the above examples, ingredients other than those recited can be added to achieve a desirable pharmaceutical effect. This invention provides a composition that is relatively simple to prepare and to administer, and it has been found effective in accomplishing its desired purpose.

Although particular formulations have been shown and described above, modifications may be made, and it is intended in the claims to cover all modifications which come within the spirit and scope of the invention.

REFERENCES

1. I. J. Goldstein and C. E. Hayes. The lectins: Carbohydrate-binding proteins of plants and animals. Adv. Carbohydr. and Biochem. 35 128 (1978). Academic Press.

2. N. Sharon and H. Lis. Lectins: Cell agglutinating and sugar-specific proteins. Science 177 947 (1972).

3. N. Sharon, Y. Reisner, A. Ravid and A. Prujansky. Studies on the interaction of lectins with saccharides on lymphocyte cell surfaces. In "Carbohydrate - Protein Interaction" (ACS Symposium Series 88; Goldstein, Ed., Washington 1979).

4. G. A. Granger, R. A. Daynes, P. E. Runge, A. M. Prieur and E. W. B. Jeffes. Lymphocytes effector molecules and cell-mediated immune reactions. Contemp. Top. Mol. Immunol. 4 205 (1975).

5. S. J. Chen, T. C. Lee and T. C. Tung; Interferon induction in inbred BALB/C mice by abrus agglutinin. Bull. Chinese Oncol. Soc. 5 33 (1984).

6. H. Lis and N. Sharon. Lectins: Their chemistry and application to immunology. "The Antigen" Vol. IV, Chapter 7, page 429 (Academic Press. 1977).

7. J. Y. Lin, K. Y. Tserng, C. C. Chen, L. T. Lin and T. C. Tung. Abrin and Ricin: New anti-tumor substances. Nature 227 292 (1970).

8. M. Esumi-Kurisu, N. Iwata-Dohi, D. Mizuno and M. Yamazaki Inhibition of murine tumor development by the lectin wheat germ agglutinin. Gann 74 398 (1983).

9. M. Kurisu, M. Yamazaki and D. Mizuno. Induction of macrophage-mediated tumor lysis by the lectin wheat germ agglutinin. Cancer Res. 40 3798 (1980).

10. A. Mazumder, E. A. Grimm and S. A. Rosenberg. Characterization of the lysis of fresh human solid tumor by autologous lymphocyutes activated in vitro with phytohemagglutinin. J. Immunol. 130 958 (1983).

11. J. Y. Lin, W. Y. Kao, K. Y. Tserng, C. C. Chen and T. C. Tung. Effect of crystalline abrin on the biosynthesis or protein, RNA and DNA in experimental tumors. Cancer Res. 30 2431 (1970).

12. H. Lin, W. R. Bruce and M. J. Walcroft. Concanavalin A (NSC-143504): Its action on experimental tumor cells and possible use in cancer chemotherapy. Cancer Themother. 59 319 (1975).

13. T. C. Tung, T. T. Yang and H. C. Chang. The growth inhibition of S-1801 Sarcoma cells by Abrus agglutinin treatment in vivo. J. Formosan Med. Assoc. 80 1 (1981).

14. I. J. Fidler. Selection of successive tumor lines for metastasis. Nature (London) New Biol. 242 148 (1973).

15. J. Y. Lin, C. C. Chen, L. T. Lin and T. C. Tung. Inhibitory effect of abrin and Ehrlich Ascitees timor. J. Formosan Med. Assoc. 68 522 (1969).

16. G. Poste and I. J. Fidler. The pathogenesis of cancer matastasis. Nature 283 10 (1980).

17. W. Wang, M. T. Kuo, T. C. Lee, P. Y. Tsai and T. C. Tung. Effects of abrin and abrus agglutinin on the cytotoxicity of murine spleen cells. Bull. Chinese Oncology Soc. 3 173 (1982).

18. Sharon and H. Lis. Use of Lectins for the Study of Membranes. "Methods in Membrane Biology", Vol. 3,, pp. 147–186 (Korn, ed., Plenum Press, New York 1975).

I claim:

1. An orally-administrable therapeutic composition useful for the suppression of post-surgical malignment tumor metastasis in mammals in need thereof after surgery which comprises a pharmaceutically and orally-acceptable carrier and an effective amount for the suppression of post-surgical malignment tumor metastasis in mammals in need thereof after surgery, of purified lectin obtained from the seeds of an a *Abrus precatorius* selected from the group of Abrin and Abris agglutinin wherein the purified lectin is present in an amount from about 1.0 to 500 micrograms and is administrable in conjunction with or subsequent to either radiation therapy or chemotherapy.

2. The orally-administrable therapeutic composition of claim 1, wherein the purified lectin is a water-soluble powder.

3. The orally-administrable therapeutic composition of claim 2, wherein the water-soluble purified lectin powder is a precipitate, dialyzate, adsorbate and eluate.

4. The orally-administrable therapeutic composition of claim 1, wherein the purified lectin is abrin.

5. The orally-administrable therapeutic composition of claim 4, wherein the abrin is present in an amount from about 1.0 to about 20.0 micrograms.

6. The orally-administrable therapeutic composition of claim 4, wherein the abrin is present in an amount from about 2.0 to about 5.0 micrograms.

7. The orally-administrable therapeutic composition of claim 1, wherein the purified lectin is abris agglutinin.

8. The orally-administrable therapeutic composition of claim 7, wherein the abris agglutinin is present in an amount from about 1.0 to about 500 micrograms.

9. The orally-administrable therapeutic composition of claim 7, wherein the abris agglutinin is present in an amount from about 50 to about 200 micrograms.

10. A method for the suppression of post-surgical malignant tumor metastasis which comprises administering orally to a mammal in need thereof after surgery a therapeutic composition comprising a pharmaceutically and orally-acceptable carrier and an effective amount for the suppression of post-surgical malignant tumor metastasis in mammals in need thereof after surgery, of purified lectin obtained form the seeds of an *Abrus precatorius* selected from the group of Abrin and Abris agglutinin, wherein the purified lectin is present in an amount from about 1.0 to 500 micrograms and is administrable in conjunction with or subsequent to either radiation therapy or chemotherapy.

11. The method of claim 10 wherein the purified lectin is administrable once daily.

12. The method of claim 10, wherein the purified lectin is Abrin.

13. The method of claim 12, wherein the daily oral dose is between about 1.0 and about 20 micrograms.

14. The method of claim 12, wherein the daily oral dose is between about 2.0 and about 5.0 micrograms.

15. The method of claim 10, wherein the purified lectin is Abris agglutinin.

16. The method of claim 15, wherein the daily oral dose is between about 1.0 and about 500 micrograms.

17. The method of claim 15, wherein the daily oral dose is between about 50 and about 200 micrograms.

18. The method of claim 10, wherein the orally-administrable therapeutic composition is administered both in conjunction with and subsequent to either radiation therapy or chemotherapy.

19. The method of claim 18, wherein the orally-administrable therapeutic composition is administered both in conjunction with and subsequent to both radiation therapy and chemotherapy.

20. The method of claim 19, wherein the orally-administrable therapeutic composition is administered either in conjunction with or subsequent to both radiation therapy and chemotherapy.

* * * * *